United States Patent [19]
Goble et al.

[11] Patent Number: 5,350,380
[45] Date of Patent: Sep. 27, 1994

[54] METHOD FOR SECURING A LIGAMENT REPLACEMENT IN A BONE

[75] Inventors: E. Marlowe Goble, Logan, Utah; Jerry L. Lower, Bourbon, Ind.

[73] Assignee: Depuy Inc., Warsaw, Ind.

[21] Appl. No.: 4,987

[22] Filed: Jan. 15, 1993

[51] Int. Cl.⁵ .............................. A61F 5/04
[52] U.S. Cl. ..................... 606/80; 606/98; 606/102; 606/104; 623/13
[58] Field of Search ............ 606/98, 97, 96, 72, 606/73, 75, 102, 104, 80, 86, 87, 88; 623/13; 408/241 G

[56] References Cited

U.S. PATENT DOCUMENTS

| | | |
|---|---|---|
| 4,738,255 | 4/1988 | Goble et al. |
| 4,772,286 | 9/1988 | Goble et al. ............ 623/13 |
| 4,901,711 | 2/1990 | Goble et al. ............ 606/98 |
| 4,950,270 | 8/1990 | Bowman et al. ......... 606/72 |
| 4,952,213 | 8/1990 | Bowman et al. ......... 606/79 |
| 4,985,032 | 1/1991 | Goble ....................... 606/96 |
| 5,013,316 | 5/1991 | Goble et al. ............ 606/72 |
| 5,108,398 | 4/1992 | McQueen et al. ....... 606/62 |
| 5,112,337 | 5/1992 | Paulos et al. ............ 606/96 |
| 5,139,520 | 8/1992 | Rosenberg ............... 623/13 |
| 5,163,940 | 11/1992 | Bourque ................... 606/96 |

OTHER PUBLICATIONS

M. Kurosaka, "The Crucial Choice for Winning Results", DePuy ®, 1989, six pages.

*Primary Examiner*—Stephen C. Pellegrino
*Assistant Examiner*—Guy V. Tucker
*Attorney, Agent, or Firm*—Barnes & Thornburg

[57] ABSTRACT

A method is provided for anchoring a replacement ligament in a bone. The method includes the steps of drilling a first hole through the bone with a drill to form a ligament tunnel, and drilling a second hole in the bone at an angle relative to the ligament tunnel using the drill inside the ligament tunnel as a reference to establish the position of the second hole. The method also includes the step of inserting a transverse pin through the second hole to secure the replacement ligament to the bone.

14 Claims, 6 Drawing Sheets

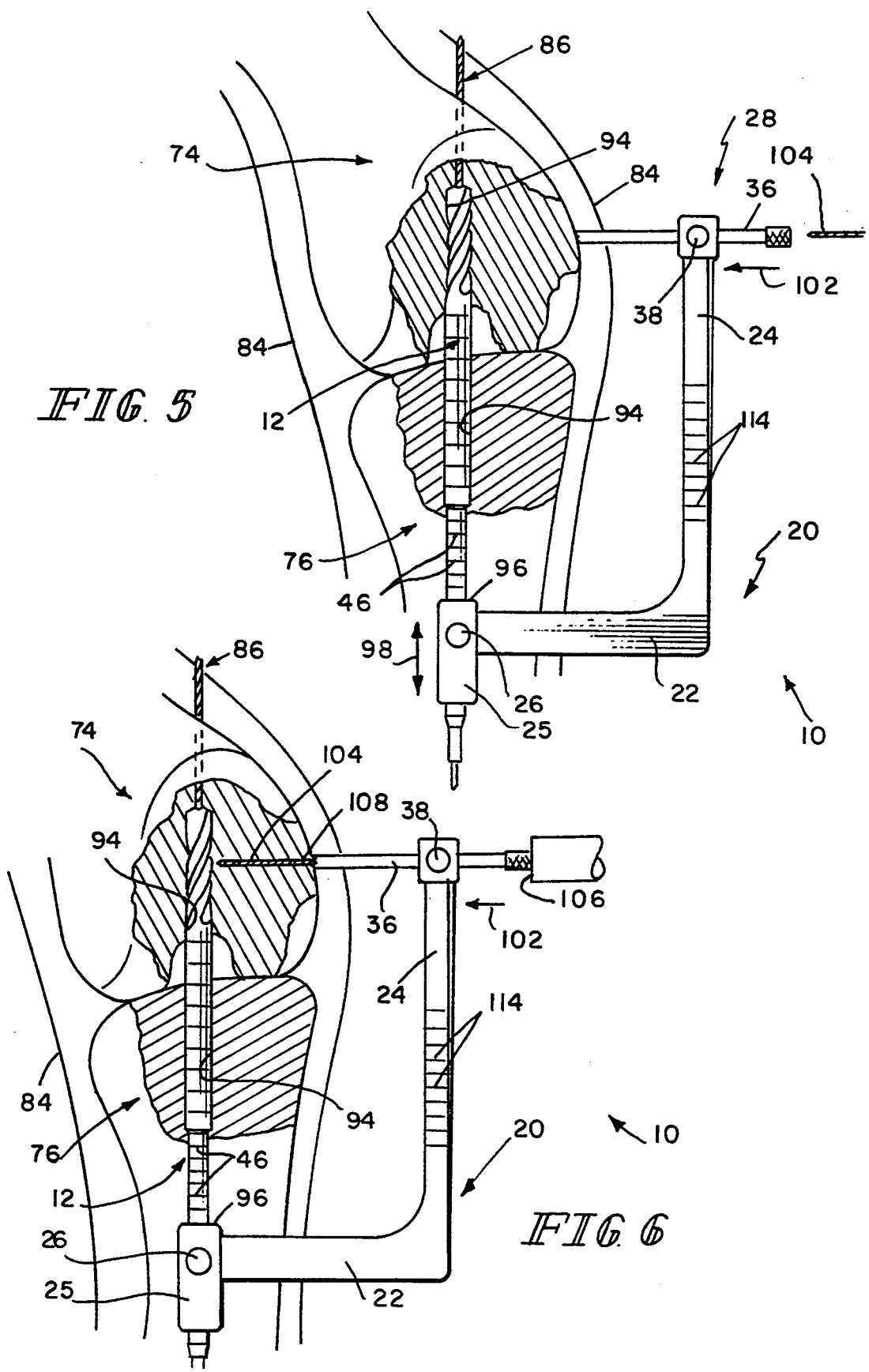

METHOD FOR SECURING A LIGAMENT REPLACEMENT IN A BONE

BACKGROUND OF THE INVENTION

1. Field of the Invention

The present invention relates to the anchoring of ligament replacements or soft tissue in bone tunnels, and more particularly to a method for locating and installing a transverse pin for holding a ligament replacement in a tunnel with the pin intersecting the tunnel and the ligament replacement. In the replacement of an anterior cruciate ligament (ACL), for example, a tunnel is drilled upwardly through the tibia plateau upwardly into the distal end of the femur. Typically, the tunnel entry point is the anterior portion of the tibia below the tibia plateau. These tunnels are typically located initially by inserting or drilling a guide pin, commonly called a K-wire, upwardly into the tibia and then upwardly into the femur while the tibia and femur are held in a desired and appropriate location to accommodate an ACL replacement. The tunnel is essentially located so that the replacement ligament is in a position to function as the replaced ACL. The K-wire or guide pin is used because it is small diameter and the surgeon can inspect the location of the K-wire and reinsert it if it is not well located without damaging the bone structure to any significant extent. It will be appreciated that the position of the K-wire may be inspected by arthroscopic techniques as well as by X-ray or other imaging approaches.

Also, typically, once the K-wire is properly positioned, a cannulated drill, sometimes referred to as a drill/reamer, is placed over the K-wire and driven upwardly to form the tunnel using the K-wire as the guide for the drill.

The method of the present invention utilizes the drill which forms the tunnel while it is in the tunnel as the control member for locating and installing the transverse pin for holding the ligament replacement in the tunnel within the femur. Specifically, within the method of the present invention, a drill guide is installed on the drill used in the tunnel drilling step, the drill guide being selectively rotatable about the axes of the drill and the guide pin and also selectively longitudinally movable along the axis of the drill appropriately to position the drill guide.

The method of the present invention contemplates installing such a transverse pin from a point outside the femur to extend transversely inwardly to the tunnel in the femur and to intersect the tunnel and the ligament replacement inserted therein.

2. The Prior Art

The prior art includes several different types of drill guides for forming tunnels in the femur and tibia for anchoring ligament replacements. One example is U.S. Pat. No. 4,901,711 which shows such a drill guide which mounts on the K-wire after it is inserted into the knee joint. The K-wire exits the knee joint at a point below the tibia and at another point above the femur. The drill guide of the '711 patent is journalled on the K-wire so that the guide is rotatable about the axis of the K-wire. The guide then has a drill sleeve which moves longitudinally parallel to the axis of the K-wire to a selected point to locate a transverse anchoring pin. The method of the present invention is an improvement over the method shown in the '711 patent because the guide is mounted only below the tibia plateau on the shank of the tunnel drill and, of course, the tunnel itself is drilled before the guide used. Using the method of the present invention, the tunnel may be located and drilled upwardly to a point terminating the tunnel in the femur at a preselected point. This preselected point is established on the drill itself such that the drill guide, when mounted on the drill, and moved to an appropriate scale point on the drill, will locate the transverse pin at an appropriate location below the uppermost end of the tunnel.

Another example is U.S. Pat. No. 4,985,032 which shows a drill guide for locating transverse pins for holding ligaments in tunnels formed in knee joints, particularly to replace the ACL. The U-shaped guide of the '032 patent is used with one leg of the guide inserted upwardly through the tunnel after the drill is removed. Use of the U-shaped guide of the '032 patent requires extra steps which are eliminated by using the tunnel drill itself as a mount for the drill guide. The tunnel drill of the present invention is provided with scale means so that the surgeon will know exactly where the uppermost end of the drill and tunnel are and where the transverse pin has to be located in the femur properly to intersect any ligament replacement placed in the tunnel and pulled upwardly to that innermost end.

BRIEF DESCRIPTION OF THE INVENTION

The present invention, therefore, relates to a method for locating and installing a transverse pin for holding a ligament replacement in a tunnel formed in adjacent jointed bones with the pin intersecting the tunnel and the ligament replacement which is inserted into the tunnel. The method comprises the steps of inserting a guide pin such as a K-wire through the adjacent bones to define the centerline of the proposed tunnel, drilling the tunnel with a cannulated drill using the guide pin as a center guide, installing a drill guide on the drill used in the tunnel drilling step, the drill guide being selectively rotatable about the axes of the drill and the guide pin and selectively longitudinally positionable along the drill to position a transverse guide opening provided by the drill guide relative to the tunnel properly to intersect the ligament replacement in one of the adjacent bones in the tunnel. Illustratively, and preferably, once the drill guide is placed on the drill, it may be pivotally adjusted about the drill and longitudinally along the drill to find the desired anatomical location for inserting the transverse pin into the tunnel. The illustrative and preferred drill and drill guides are provided with scale means for use in locating the drill guide. Then, the steps comprise drilling transversely into the bone to provide the transverse guide hole and inserting the transverse pin through the guide hole, the tunnel, the ligament replacement therein and on into the opposite side of the tunnel to anchor the ligament replacement in the tunnel.

Further, in accordance with the method of the present invention, the drill guide may be used to locate and install a second transverse pin in the adjacent bone intersecting the tunnel and the ligament replacement in the second bone. The further steps for installing the second pin comprise pivotally adjusting the position of the drill guide about the drill to find a desired location for inserting the second transverse pin into the adjacent bone and then drilling transversely into the adjacent bone to provide a transverse guide hole for use in inserting the transverse pin.

It will be appreciated that, for the most part, most of the ligaments being replaced by orthopedic surgeons are the ACLs which are commonly injured in sporting events. The method of the present invention may be ideally used for installing transverse pins to anchor an ACL replacement ligament with the method comprising the steps of inserting a guide pin through an anterior portion of the tibia upwardly through the tibia plateau and upwardly into the distal end of the femur to define a centerline of the tunnel, drilling the tunnel with a cannulated drill using the guide pin as a center guide and terminating the tunnel in the femur at a preselected point, installing a drill guide over the drill used in the tunnel drilling step, the drill guide being rotatable about the axes of the drill and the guide pin, the guide having a journal end mounted on the drill and an upwardly extending arm terminating with a transverse guide opening having an axis intersecting the axes of the guide pin and tunnel drill, adjusting the position of the drill guide longitudinally on the drill to position the axis of the transverse guide opening relative to the uppermost end of the tunnel corresponding to the preselected point at the upper end of the drill properly to intersect the ligament replacement in the tunnel, and then using the drill guide, as described above, to locate and install a transverse pin in the femur to anchor the ACL replacement within the femur and, if desired, to use the same drill guide as discussed above to locate and install a transverse pin in the tibia to anchor the ACL replacement within the tunnel in the tibia.

A number of different types of ligament replacements are contemplated by the method of the present invention. Typically, a surgeon will obtain a ligament replacement by removing a portion of the patella tendon leaving a bone plug on each end of the patella tendon for anchoring within the tunnel. In such a case, the transverse pins will penetrate through the bone plugs to anchor each end of the patella tendon in the tunnel leaving the intermediate portion of the tendon to serve as a ligament replacement. The use of patella tendons in tunnels for ACL replacement is well known and well described in the literature. It is common to anchor the bone plugs of the patella tendon replacement with what are known as Kurosaka interference fixation screws. These fixation screws may be threaded axially into the tunnels to wedge the bone plugs into position to be fixed within the tunnels.

Other types of ligament replacements are being considered and some are actually being used. In this specification and in the appended claims, the term "ligament replacement" is intended to refer to any material which may be harvested from the patient, from cadavers, or from animals or any material which may be made, for instance, from plastic or metal to provide a ligament function. Further, in this specification and in the appended claims, the term "intersecting the ligament replacement" is intended to refer to all types of intersection and/or connection which may be accomplished by extending a pin transversely through a tunnel. For example, as indicated, such a transverse pin may extend through the bone plug provided on the end of a patella tendon. The transverse pin may extend through the soft tissue itself or through a loop formed in the soft tissue. Still further, the word "transverse" is intended to mean an intersection or crossing which may or may not be perpendicular to the tunnel axis.

An object of the invention, therefore, is to provide a method for anchoring a replacement ligament in a bone, the method comprising of steps of drilling a first hole through the bone with a drill to form a ligament tunnel, drilling a second hole in the bone at an angle relative to the ligament tunnel using the tunnel drill inside the ligament tunnel as a reference to establish the position of the second hole, and then inserting a transverse pin through the second hole to secure one end of the replacement ligament to the bone.

Still another object of the present invention is to provide such a method of installing a transverse pin for holding a ligament replacement in a tunnel formed in a bone with the pin intersecting the tunnel and the ligament replacement, the method comprising the steps of locating a drill sleeve at a desired anatomical location for inserting the transverse pin into the bone to intersect the ligament replacement in the tunnel, drilling through the drill sleeve and into the bone transversely to the tunnel at the desired anatomical location at a predetermined distance short of the tunnel with a first drill having a first diameter to provide a transverse guide hole, inserting a second drill having a second diameter larger than the first diameter through the drill sleeve and into the guide hole, installing a soft tissue protector over the second drill, drilling through the bone, the tunnel, the ligament replacement and on into the bone on an opposite side of the tunnel using the second drill extending through the soft tissue protector, removing the second drill leaving the soft tissue protector and inserting the transverse pin through the soft tissue protector, the guide hole, the tunnel and the ligament replacement therein, and on into the bone on an opposite side of the tunnel to anchor the ligament replacement in the bone.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 5 is a diagrammatical illustration of the knee of FIGS. 3 and 4 in which the knee has been canted and the drill guide of FIG. 1 has been installed onto an end of the tunnel drill for aligning the position of a transverse pin for securing the replacement ligament inside the tunnel;

FIG. 6 is a view similar to FIG. 5 in which a first drill is used to form a transverse guide hole through the femur;

DETAILED DESCRIPTION OF THE DRAWINGS

Figure 1:
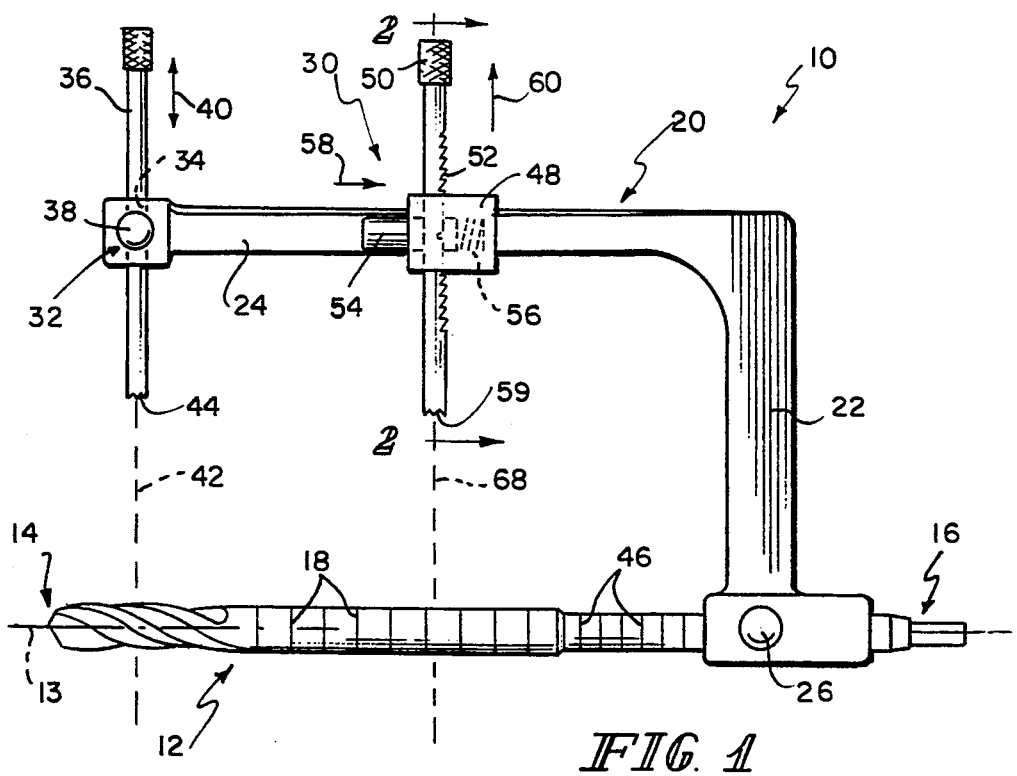
FIG. 1 is an elevational view of a drill guide apparatus of the present invention for aligning and installing transverse pins through a tunnel in a bone using a drill which forms the tunnel as a reference.
Figure 2:
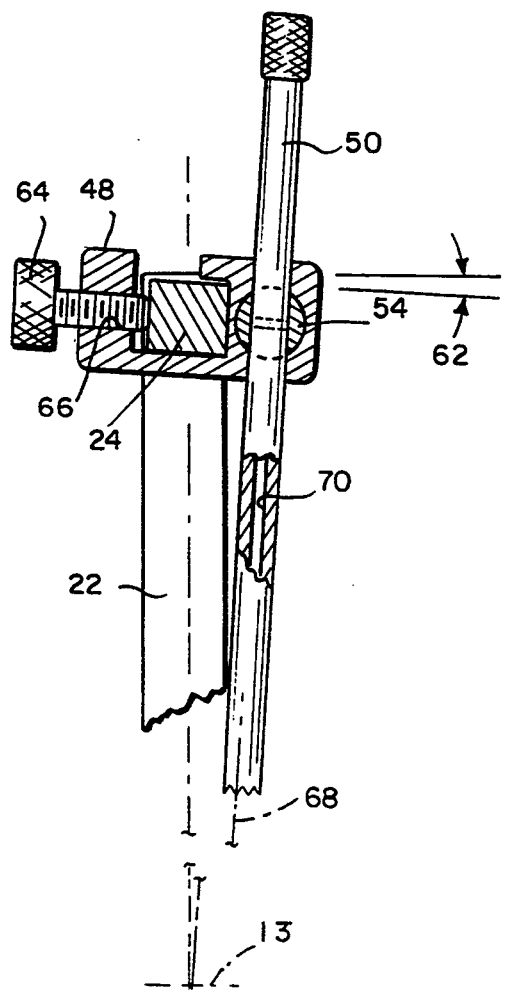
FIG. 2 is a sectional view taken along lines 2—2 of FIG. 1 illustrating a tibia drill guide and drill sleeve aligned at an angle to intersect an axis of the tunnel drill.

Referring now to the drawings, FIGS. 1 and 2 illustrate a drill guide apparatus 10 of the present invention. A tunnel drill 12 is used to form a tunnel through a bone such as through the tibia and femur to replace the anterior cruciate ligament in a knee joint. Tunnel drill 12 includes a first end 14 for cutting through the bone and a second end 16 for attachment to a driver. Drill 12 includes a set of depth indicators or marks 18 which are labeled with numbers to indicate the distance from the marks 18 to the tip of first end 14 of drill 12. Drill guide apparatus 10 is adapted to be rotatably and slidably coupled to second end 16 of drill 12. Drill guide apparatus 10 illustratively includes a generally L-shaped body portion 20 having a first arm 22 extending generally perpendicular to drill 12 and a second arm 24 which extends away from first arm 22 in a direction generally parallel to drill 12. An end of first arm 22 is slidably and rotatably coupled to second end 16 of drill 12 by a spring-loaded cog 26 inside connector body 25. Cog 26 can be depressed to permit sliding movement of body portion 20 of drill guide apparatus 10 longitudinally relative to drill 12. When cog 26 is released, a spring biases cog 26 against annular grooves formed in drill 12 to secure the body portion 20 in a set position relative to drill 12.

Drill guide apparatus 10 includes a femur drill guide 28 and a tibia drill guide 30. Drill guide apparatus 10 is illustratively configured to align and install transverse pins through the femur and tibia which intersect the axis of the tunnel drilled by drill 12 and the replacement ligament located inside the tunnel. Femur drill guide 28 is illustratively integrally formed on a distal end 32 of body portion 20. Transverse guide opening 34 is provided in distal end 32 of body portion, and a drill sleeve 36 extends through transverse guide opening 34. Drill sleeve 36 is slidably coupled to distal end 32 of body portion 20 by a spring-loaded cog 38. Spring-loaded cog 38 may be depressed to permit slidable movement of drill sleeve 36 in the direction of double-headed arrow 40. Drill sleeve 36 includes a plurality of teeth (not shown) on a side opposite the illustrated side in FIG. 1. When cog 38 is released, a spring biases cog 38 against the teeth to secure the drill sleeve in a predetermined position relative to body portion 20. The teeth and cog apparatus provide ratchet means for adjusting the position of drill sleeve 36 relative to body portion 20. Advantageously, drill sleeve 36 may be adjusted relative to body portion 20 using a single hand. This permits accurate and rapid adjustment of the position of drill sleeve 36 as discussed in detail below. Drill sleeve 36 is formed to include a central bore therethrough having an axis 40 which intersects axis 13 of drill 12. The bone engaging end of drill sleeve 36 includes teeth 44 which cut into bone to help hold the position of drill sleeve 36 relative to a bone.

Drill 12 includes a second set of cross hatch markings 46 which provide indicia of the position of axis 42 of drill sleeve 36 relative to the tip of first end 14 of drill 12. The tip of first end 14 of drill 12 corresponds to the position of the end of the tunnel inside the bone. Therefore, a surgeon can use the indicia marks 46 to establish the position for the transverse pin a predetermined distance from the end of the tunnel.

Drill guide apparatus 10 also includes a tibia drill guide 30. Tibia drill guide 30 includes a mounting block 48 and a drill sleeve 50. Drill sleeve 50 includes a plurality of teeth or saw toothed serrations in drill sleeve 36. Mounting block 48 includes a spring-loaded cog 54 and a spring 56 which biases the cog 54. When cog 54 is depressed in the direction of arrow 58, drill sleeve 50 is released to permit slidable movement of drill sleeve 50 relative to body portion 20 in the direction of double-arrow 60. When cog 54 is released, spring 56 biases cog 54 against the teeth 52 of drill sleeve 50 to hold drill sleeve 50 in place relative to body portion 20. In other words, drill sleeve 50 is ratcheted to body 20 in the same manner as drill sleeve 36.

Ratchet control of drill sleeves 36 and 50 provides an advantage of the present invention. This ratcheting feature may be incorporated onto other guide mechanisms which include a guide arm. A push button release (cogs 38 and 54) permits drill sleeves 36 and 50 to slide back and forth relative to arm 24. This provides better control of movement of drill sleeves 36 and 50 when compared to drill sleeves which are coupled to guide arms by a screw fastener. The ratchet mechanisms also provide a more positive lock for drill sleeves 36 and 50 against the bone. The ratchets provide a one-way lock and can be pushed toward the bone but not pulled away from the bone. Therefore, they can be moved with one hand. The ratchet mechanism also keeps a tight engagement between teeth 44 and 46 of drill sleeves 36 and 50, respectively, against the bone.

As illustrated in FIG. 2, arm 24 of body portion 20 is twisted a predetermined angle relative to arm 22 illustrated by angle 62. Illustratively, angle 62 is about 5.8 degrees. Body portion 48 is slidably coupled to arm 24 by a threaded bolt 64 extending through a threaded aperture 66 in body portion 48. By providing the twisted arm 24, an axis 68 defined by longitudinal bore 70 of drill sleeve 50 intersects axis 13 of drill 12.

Drill guide apparatus 10 is used to align and install transverse pins into a tunnel formed in a bone. Operation of the drill guide apparatus 10 of the present invention is illustrated in FIGS. 3–11. The drill guide apparatus 10 is particularly suited for replacement of an anterior cruciate ligament in a knee joint. However, it is understood that the drill guide apparatus may be used to replace other ligaments in a bone. Detailed operation of the drill guide apparatus 10 will be explained with reference to replacing the anterior cruciate ligament in a knee joint.

Figures 3, 4:
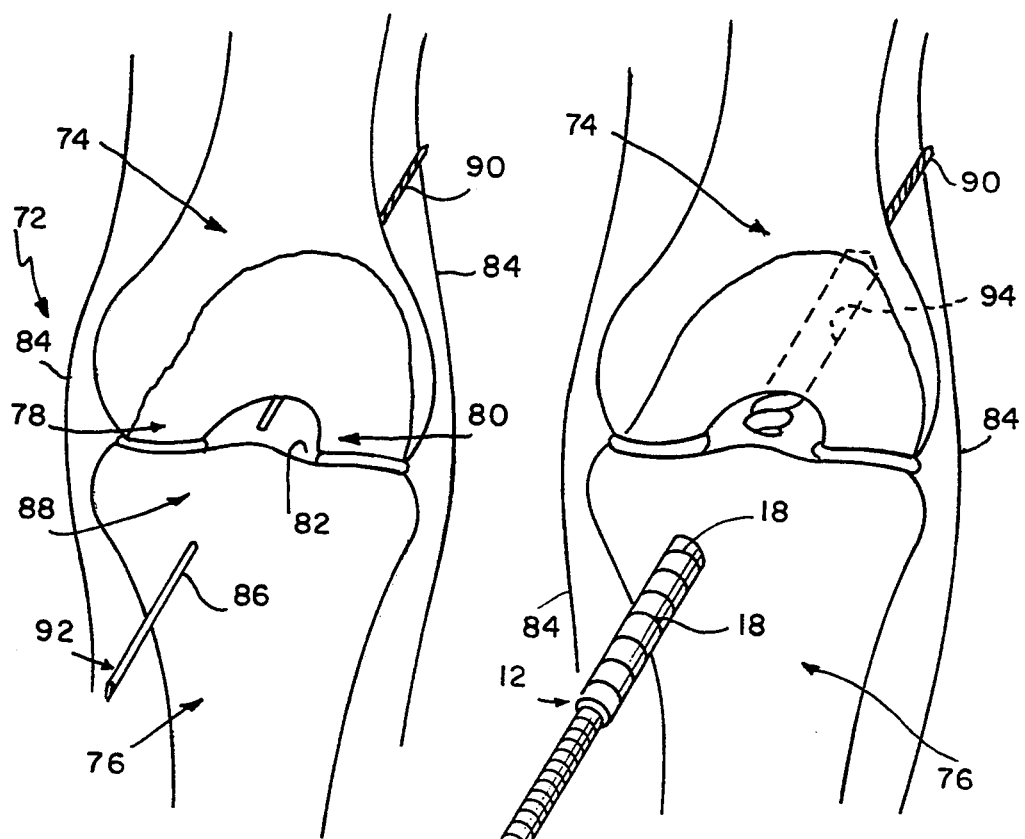
FIG. 3 is a diagrammatical illustration of a front view of a knee in which the anterior cruciate ligament is to be replaced illustrating a guide pin inserted through an anterior portion of the tibia upwardly through the tibia plateau and through a distal end of a femur to establish the position of a tunnel to be formed through the knee.
FIG. 4 is a diagrammatical illustration similar to FIG. 3 in which a tunnel drill has been inserted over the guide pin in the knee to form the tunnel for receiving the replacement ligament.
Figure 7:
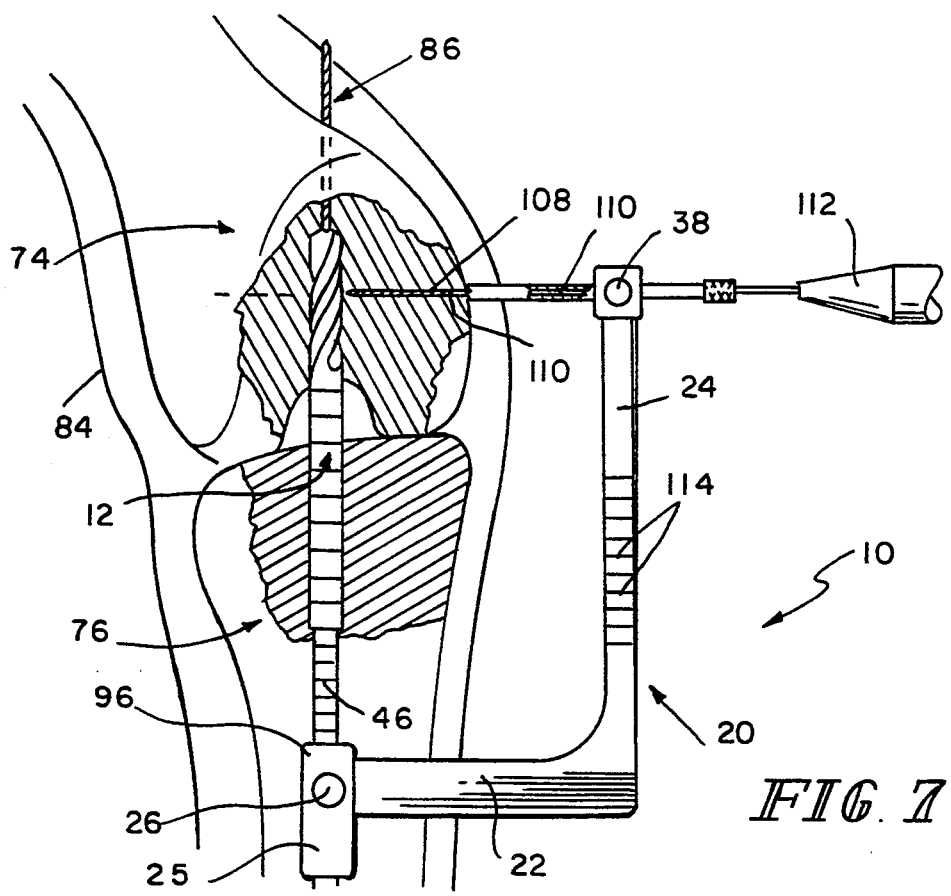
FIG. 7 is a diagrammatical illustration similar to FIGS. 5 and 6 in which a second drill is inserted through the drill sleeve to a position below the arm of the drill guide.
Figure 8:
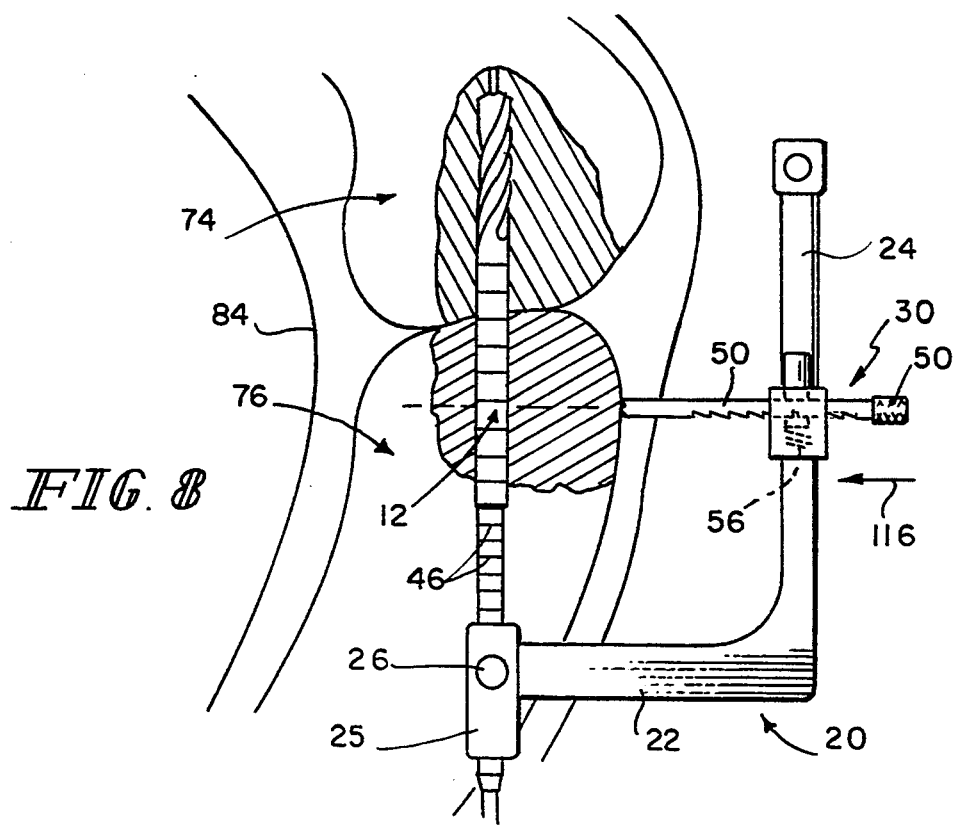
FIG. 8 is a diagrammatical illustration of the knee in which the knee has been rotated 90° with respect to FIGS. 3 and 4 and a tibia drilling guide is used to establish the desired anatomical position for installing a transverse pin through the tunnel in the tibia.
Figure 9:
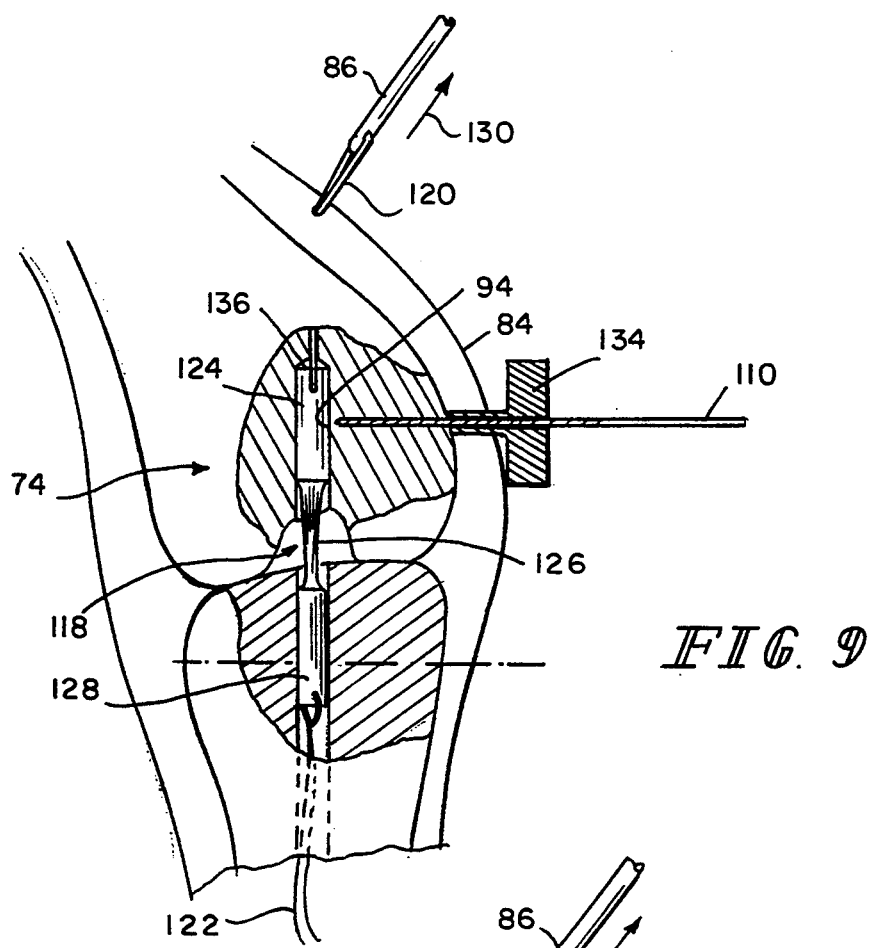
FIG. 9 is a diagrammatical view similar to FIGS. 5-7 in which the tunnel drill and drill guide have been removed, a replacement ligament has been inserted into the tunnel, and a soft tissue protector has been installed over the second drill remaining in the femur.

As illustrated in FIG. 3, a knee joint 72 includes a femur bone 74 and a tibia bone 76. Condyles 78 and 80 of femur 74 articulate against a tibial plateau during movement of knee 72. FIGS. 3–11 also diagrammatically illustrate soft tissue 84 surrounding the knee. During replacement of the anterior cruciate ligament, a tunnel is formed through the knee joint at an angle to replicate the position of the natural anterior cruciate ligament. Therefore, the first step for replacing the anterior cruciate ligament of a knee is to form the tunnel through the knee 72 for receiving a replacement ligament. The first step for drilling the tunnel is typically to install a K-wire or guide pin 86 through an anterior portion 88 of tibia 76 upwardly through tibial plateau 82 and on upwardly through the distal end of femur 74. The position of guide pin 76 can be viewed using endoscopes inserted into the knee or using x-rays or fluoroscopes. If the surgeon is unhappy with the position of guide pin 86, it can be removed and re-inserted without causing substantial damage to knee 72. This because guide pin 86 cuts only a relative thin hole through knee joint 72. Guide pin 86 includes a first end 90 equipped with a drill point for cutting the bone and a second end 92 which includes an aperture 93 which permits the guide pin 86 to pull the replacement ligament through the tunnel as discussed in detail below.

After the surgeon has positioned the guide pin 86 at a desired location for the center line of the tunnel, drill 12 is used to form the tunnel in knee joint 72. Preferably, drill 12 is cannulated so that drill 12 can pass over guide pin 86 to cut tunnel 94 through knee joint 72. Therefore, guide wire 86 provides the center line for tunnel 94. FIG. 4 illustrates drill 12 which has been driven into knee joint 72 along the path established by guide wire 86 to form tunnel 94.

After tunnel 94 is formed inside knee joint 72, the surgeon leaves drill 12 in place in the knee. The driver is removed from drill 12 and drill guide apparatus 10 is inserted over second end 16 of drill 12. A surgeon can read the depth of insertion of drill 12 into the bone by reading the depth indicia marks 18 on drill 12. This gives the surgeon an estimate of the length of the replacement ligament required. The replacement ligament is typically harvested in a conventional manner using known techniques. For instance, a portion of the patellar tendon can be harvested to provide tissue for replacing the anterior cruciate ligament, the tissue being a length of tendon with a bone plug at each end. Other methods for harvesting bone can also be used. In addition, ligament material may be looped over pins within tunnel 94 as discussed in more detail below.

After the replacement ligament is harvested or obtained, a surgeon can estimate the distance from an end of the bone plug which would be optimum for inserting the transverse pin. Drill guide apparatus 10 permits the position of the pins to be aligned at about the optimum position. By depressing cog 26, the drill guide apparatus 10 can slide back and forth in the direction of double-headed arrow 98 on drill 12.

If the surgeon knows the optimum location to insert the transverse pin, the surgeon sets the position of drill guide on drill 12 to that known distance on indicia marks 46. For instance, if the surgeon wants to position the transverse pin 25 mm from the end of the replacement ligament, the surgeon slides drill guide apparatus 10 until a top edge 96 of connector block 25 is aligned with the measurement mark 46 corresponding to 25 mm. This positions the axis 42 of femur drill sleeve 36 at a distance 25 mm from the end 14 of drill 12. Since the end 14 of drill 12 will correspond to the end of the replacement ligament, the axis 42 of drill sleeve 30 would be 25 mm from the end of the replacement ligament. Therefore, the position of drill guide apparatus 10 can be selectively adjusted longitudinally on the drill to position the axis of the transverse guide opening and drill sleeve 36 relative to the uppermost end of the tunnel corresponding to a preselected point at the upper end of the drill so that the axis will intersect ligament replacement in the tunnel.

Figure 11:
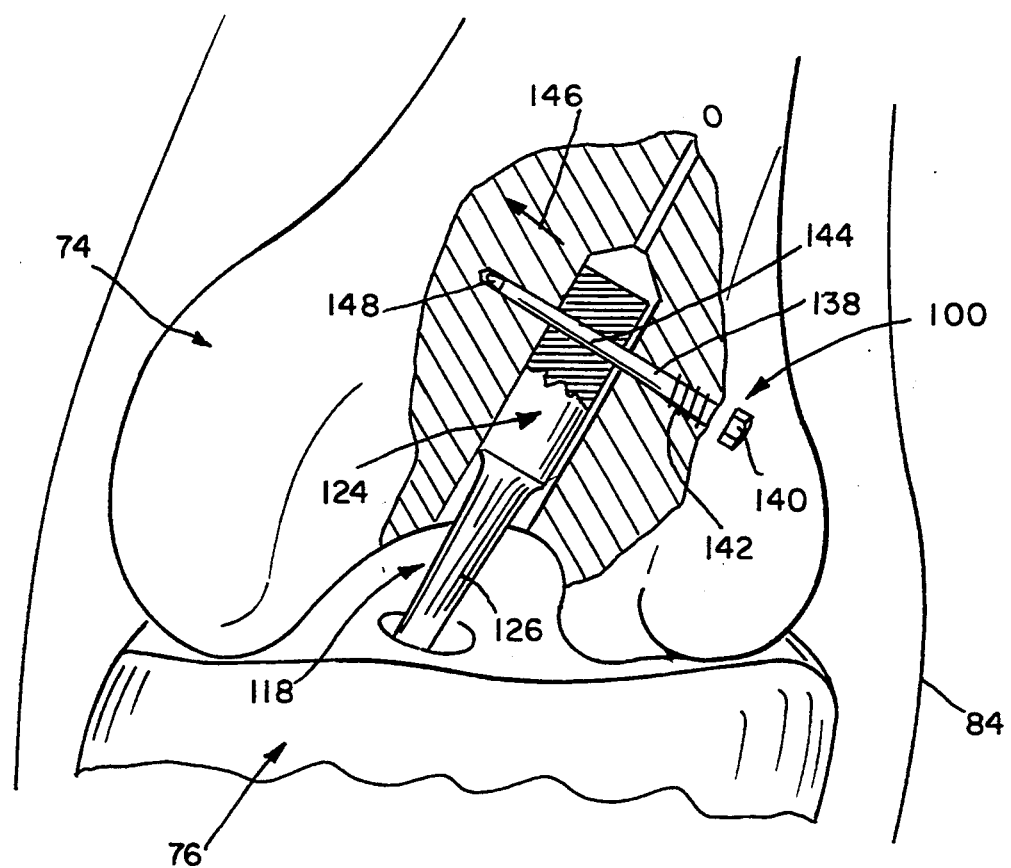
FIG. 11 is a diagrammatical illustration with portions broken away illustrating a transverse pin installed through the hole formed by the second drill to extend through the femur, through the tunnel and the replacement ligament therein, and on into the femur on the opposite side of the tunnel to secure the replacement ligament to the femur.

After the longitudinal position of drill guide apparatus 10 is set, the next step is to rotate or pivot drill guide apparatus 10 about the axis of drill 12 and guide pin 86 to position drill sleeve 36 at a desired anatomical location for inserting the transverse pin into the femur. Typically, this location is on the lateral epicondyle 100 as best illustrated in FIG. 11.

After the desired anatomical position of the transverse pin has been selected, drill sleeve 36 is ratcheted toward femur in the direction of arrow 102. Drill sleeve 36 passes through a small incision in the soft tissue 84 and engages the surface of femur 72 as illustrated in FIG. 5. A first drill 104 is then used to drill a first hole through femur 74 using drill sleeve 36 as a guide. First drill 104 has a first diameter which is illustratively 2.4 mm. Drill 104 forms a transverse hole in femur 74. A stop 106 (see FIG. 6) is coupled to drill 104 so that drill 104 drills only a predetermined distance into femur 74. Stop 106 prevents drill 104 from hitting drill 12 located in tunnel 94. Therefore, stop 106 causes drill 104 to stop short of tunnel 94 and provides a transverse guide hole 108 through femur 74. The first drill 104 is then removed from drill sleeve 36.

A second drill 110 is then inserted into transverse guide hole 108. Second drill 110 has a second diameter which is slightly larger than the first diameter. Illustratively, the diameter of second drill 110 is about 2.5 mm. Second drill 110 is tapped through drill sleeve 36 and into transverse guide hole 108 with an insertion device 112 which inserts second drill 110 to a depth so that an end of second drill 110 is located beyond end 32 of body portion 20. Drill sleeve 36 is then removed from body portion 20 leaving drill 110 in femur 74.

If it is desired to secure the ligament replacement in the tibia with a transverse pin, the drill guide apparatus 10 can be rotated about axis 13 of drill 12 to another position for forming the hole for insertion of the tibia transverse pin. Body portion 20 of drill guide apparatus 10 includes a measurement scale including labeled marks 114. These marks 114 indicate the distance from axis 42 of drill sleeve 36 to axis 68 of drill sleeve 50. Therefore, a surgeon can measure the distance from the optimum location of the transverse pin in the femoral portion of ligament replacement to the optimum position of the transverse pin in the tibial portion of the replacement. Once this distance is known, the surgeon can set the position of tibial drill guide 30 at a location aligned with the mark 114 corresponding to that distance. Once the position of tibia drill guide 30 is set, drill guide apparatus 10 is rotated to align drill sleeve 50 with a desired anatomical location for inserting transverse pin into tibia 76. Drill sleeve 50 is then ratcheted in the direction of arrow 115 until teeth 59 engage tibia 76. After the drill sleeve 50 is in contact with tibia 76, the surgeon follows the same steps for inserting the drills 104 and 110 into the femur illustrated in FIGS. 6 and 7. First, the small drill 104 is used with a stop 106 to form a transverse guide hole in tibia 74. The guide hole in tibia 74 stops just short of hitting drill 112. A third drill identical to the drill 110 remaining in femur 74 is then tapped into transverse guide hole using instrument 112 illustrated in FIG. 7. After the larger diameter drill is tapped into the guide holes in tibia 76, the drill guide apparatus 10 and tunnel drill 12 are removed.

In one method of the present invention, a bone-ligament-bone replacement ligament 118 has sutures 120 and 122 attached to opposite ends. In the embodiment illustrated in FIGS. 9-11, the replacement ligament 118 includes a first bone block 124, an intermediate ligament 126, and a second bone block 128. Sutures 120 may be secured in aperture 93 in guide pin 86 so that replacement ligament 118 can be pulled into tunnel 94 as guide pin 86 is removed from tunnel 94 in the direction of arrow 130. The sutures 120 are used to hold a top edge 132 of replacement ligament 118 at a location adjacent the uppermost part of tunnel 94.

A soft tissue protector 134 is then inserted over drill 110 which remains in femur 74. Soft tissue protector 134 protects soft tissue 84 from being wrapped around drill 110. In addition, soft tissue protector 134 includes a handle (not shown) and teeth which can be tapped slightly into the femur 74 to mark the position of the guide hole formed by drill 110.

Figure 10:
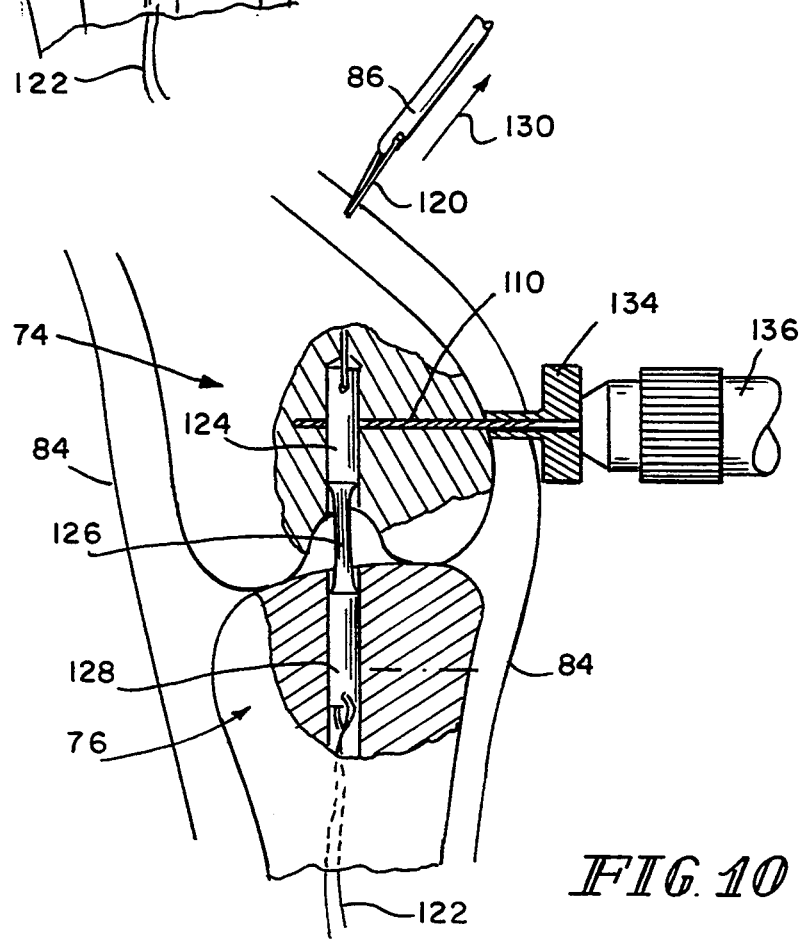
FIG. 10 is a diagrammatical illustration similar to FIG. 9 in which the second drill is used to form a hole through the femur, through the tunnel and the replacement ligament therein, and on into the femur on an opposite side of the tunnel.

The next step of the invention is illustrated in FIG. 10. A driver 136 is used to drive drill 110 further into femur 74, through tunnel 94, through the bone block 124 of replacement ligament 118 located inside tunnel 124, and on into the femur 74 on an opposite side of tunnel 94 from driver 136.

The drill 110 is then removed, leaving soft tissue protector 134 in place. Therefore, after removing drill 110, the soft tissue protector 134 continues to mark the location of hole 108 drilled through femur 74. A transverse pin is then inserted through soft tissue protector 134 and into hole 108. A hex driver is used to drive transverse pin into femur 74. Transverse pin 138 is illustrated in FIG. 11.

Although many types of transverse pins may be used with the present invention, the preferred embodiment includes an external hex head 140, a threaded section located adjacent head 140, and a tapered, generally smooth shank 144. Tapered shank 144 applies a force in the direction of arrow 146 to bone block 124 as cross pin 138 is inserted into femur 74. This forces bone block 124 against an outer wall of femur of tunnel 94 to secure bone block 124 within femur 74 and to promote healing of bone block 124 inside femur 74. Cross pin 138 also includes a blunt tip 148 to facilitate insertion of cross pin 138 into femur 74.

Bone block 128 located inside tibia 76 can be secured in any number of ways. A Kurosaka ™ fixation screw may be inserted into an aperture formed by drill 12 to secure bone block 128 to tibia 76. In addition, sutures 122 can be secured to tibia 76 using an attachment washer.

If it is desired to use a transverse pin through bone block 128 in tibia 76, ligament replacement 118 is adjusted to the proper tension by pulling on sutures 122. The third drill located in the hole formed in tibia 76 as discussed above is then used to establish the guide hole for a second transverse pin which is inserted through the tibia and tunnel 94 and through bone block 128 and on into the tibia on an opposite side from a driver. The transverse pin is inserted into the tibia in the same manner discussed above in detail with reference to drilling and installing the transverse pin in femur 74.

Although the invention has been described in detail with reference to a certain preferred embodiment, variations and modifications exist within the scope and spirit of the invention as described and defined in the following claims.

What is claimed is:

1. A method for locating and installing a transverse pin for holding a knee ligament replacement in a tunnel with the pin intersecting the tunnel and the ligament replacement, wherein the tunnel is drilled through a tibia plateau from a point therebelow upwardly into the distal end of femur, the method comprising the steps of:

inserting a guide pin through an anterior portion of the tibia upwardly toward the femur and through the tibia plateau and upwardly into the distal end of the femur to define a centerline of the tunnel;

drilling the tunnel with a cannulated drill using the guide pin as a center guide for defining the centerline of the tunnel and terminating the tunnel in the femur at a preselected point;

installing a drill guide on the drill used in the tunnel drilling step, the drill guide being shiftable along and rotatable about the centerline axes of the drill and guide pin, said drill guide having a first arm with a journal adjacent one end thereof which journal is mounted on the drill and a second arm extending at an angle to the first arm and approximately parallel to the centerline axis and terminating with a transverse guide opening having a drill axis intersecting the centerline axes of the guide pin and tunnel drill;

shifting the position of the drill guide longitudinally on the drill to position the axis of the transverse guide opening relative to an uppermost end of the tunnel to have the axis of the transverse guide opening intersect the centerline axis at a preselected point at the upper end of the tunnel to intersect the ligament replacement when the ligament replacement is located in the tunnel;

rotating the position of the drill guide about the centerline axes of the drill and guide pin to a desired anatomical location for inserting the transverse pin into the femur;

placing a drill sleeve in the transverse guide opening and moving the drill sleeve into engagement with the femur;

using the drill sleeve as a guide for a first drill having a first diameter drilling a first guide hole into the femur transversely to the centerline axis for a predetermined distance that stop short of entry into the tunnel to provide a transverse guide hole;

removing the first drill from the first guide hole and drill sleeve and inserting a second drill having a second and larger diameter in the guide opening;

removing the drill sleeve leaving the second drill in place in the first guide hole in the femur;

removing the drill guide and the tunnel drill leaving the guide pin in position in the tunnel;

inserting the ligament replacement into the upper end of the tunnel to be intersected by a centerline axis of the transverse guide hole;

installing a soft tissue protector over the second drill to engage the femur;

using the second drill, elongating the first guide hole by continuing to drill through the femur into the tunnel and the ligament replacement therein and into the femur on an opposite side of the tunnel;

removing the second drill leaving the soft tissue protector; and inserting the transverse pin through the soft tissue protector, the first guide hole, the tunnel, the ligament replacement therein, and on into the femur on an opposite side of the tunnel to anchor the ligament replacement in the femur.

2. The method of claim 1, including locating and installing a second transverse pin in the tibia which second transverse pin intersects the tunnel and the ligament replacement, the method further comprising the steps of:

prior to the step of removing the drill guide and the tunnel drill, rotatably adjusting the position of the drill guide about the centerline axes of the drill and guide pin to a desired anatomical location for inserting the second transverse pin into the tibia;

placing a second drill sleeve in a second transverse guide opening provided on said second arm and moving the drill sleeve into engagement with the tibia;

using the second drill sleeve as a drill guide for the first drill having the first diameter and drilling into the tibia a predetermined distance short of the tunnel opening to provide a transverse guide hole in the tibia;

removing the first drill from the second drill sleeve; inserting a third drill having a diameter substantially equal to the second and larger diameter drill in the guide hole of the tibia, and after the first transverse pin has been inserted into the femur;

removing the second drill sleeve leaving the third drill in place in the guide hole in the tibia;

installing a second soft tissue protector over the third drill to engage the tibia;

using the third drill elongating the guide hole in the tibia by continuing to drill through the tibia and to the tunnel in the tibia and the ligament replacement therein and into the tibia on an opposite side of the tunnel;

removing the third drill leaving the soft tissue protector; and inserting a second transverse pin through the second soft tissue protector, the tibia guide hole, the tunnel, the ligament replacement therein and on into the tibia on an opposite side of the tunnel to anchor the ligament replacement in the tibia.

3. A method for anchoring a replacement ligament in a bone, the method comprising the steps of:

drilling a first hole through the bone with a drill to form a ligament tunnel for receiving a replacement ligament;

drilling a second hole in the bone at an angle relative to the ligament tunnel using the drill inside the ligament tunnel as a support for a drill drilling the second hole to establish the position of the second hole; inserting the replacement ligament into the ligament tunnel; and inserting a transverse pin through the second hole and replacement ligament to secure the replacement ligament to the bone.

4. The method of claim 3, further comprising the step of inserting a guide pin through the bone to establish the position of a ligament tunnel prior to the step of drilling the first hole through the bone to form the ligament tunnel.

5. The method of claim 4, wherein the drill is cannulated so that the drill passes over the guide pin to form the ligament tunnel.

6. The method of claim 3, wherein the step of drilling the second hole includes the steps of:

installing a drill guide on the drill used in the tunnel drilling step, the drill guide having a first arm with a journal end mounted on the drill and a second arm extending at an angle to the first arm and generally parallel to centerline axis of the ligament tunnel having a drill sleeve coupled thereto, the drill sleeve having a drill axis intersecting the centerline axis of the tunnel;

adjusting the position of the drill guide along the centerline axis of the tunnel to position the drill axis of the drill sleeve at a desired anatomical location for inserting the transverse pin to intersect a ligament replacement in the tunnel; and drilling a second hole into the bone using the drill sleeve as a drill guide.

7. The method of claim 6, wherein the step of drilling the second hole further includes the steps of:

passing a drill transversely through the drill sleeve and drilling a first diameter hole into the bone a predetermined distance stopping short of the tunnel to provide a transverse guide hole;

removing the first drill from the drill sleeve and inserting a second drill having a second diameter which is larger than the first diameter into the drilled guide hole;

removing the drill sleeve leaving the second drill in place in the guide hole in the bone;

removing the drill guide and the tunnel drill from the tunnel;

inserting a ligament replacement into the tunnel in the bone to be intersected by a centerline axis of the transverse guide hole;

installing a soft tissue protector over the second drill to engage the bone;

elongating the guide hole by using the second drill to continue drilling through the bone, the tunnel, the ligament replacement therein and on into the bone on an opposite side of the tunnel;

removing the second drill leaving the soft tissue protector; and inserting the transverse pin through soft tissue protector, the elongated guide hole, the tunnel, the ligament replacement therein, and on into the bone on an opposite side of the tunnel to anchor the ligament replacement in the bone.

8. The method of claim 6, wherein the step of adjusting the position of the drill guide relative to the drill includes the steps of:

adjusting the position of the drill guide longitudinally on the drill to position the centerline drill axis of the drill sleeve relative to an end of the tunnel so that the centerline drill axis of the drill sleeve intersects the ligament replacement in the tunnel at a selected position; and pivotally adjusting the position of the drill guide about the axis of the tunnel drill to position the drill sleeve at the desired anatomical location on the bone for inserting the transverse pin into the bone.

9. A method for installing a transverse pin for holding a ligament replacement in a tunnel formed in a bone with the pin intersecting the tunnel and the ligament replacement, the method comprising the steps of:

using a first drill to drill a tunnel into the bone for reception of the ligament replacement;

locating a drill sleeve at a desired anatomical location using the first drill inside the tunnel as a support to establish the position of the drill sleeve for inserting the transverse pin into the bone to intersect the ligament replacement in the tunnel;

inserting a second drill through the drill sleeve and drilling into the bone transversely to the tunnel at a desired anatomical location for a predetermined distance short of the tunnel with the second drill having a first diameter to provide a transverse guide hole;

removing the second drill and inserting a third drill having a third diameter larger than the first diameter through the drill sleeve and into the guide hole;

installing a soft tissue protector over the third drill;

removing the first drill and inserting a ligament replacement into the tunnel;

elongating the guide hole by using the third drill to drill through the bone to and through the tunnel and the ligament replacement therein and on into the bone on an opposite side of the tunnel;

removing the second drill leaving the soft tissue protector; and inserting the transverse pin through soft tissue protector, the guide hole, the tunnel, the ligament replacement therein, and on into the bone on an opposite side of the tunnel to anchor the ligament replacement in the bone.

10. A method for anchoring a replacement ligament inside a knee which includes a tibia bone and a femur bone, the method comprising the steps of:

drilling a first hole through the tibia and the femur with a drill to form a ligament tunnel therethrough for receiving a replacement ligament therein;

drilling a second hole in the femur at an angle relative to the ligament tunnel using the drill inside the ligament tunnel as a support to establish the position of the second hole;

inserting a ligament replacement into the ligament tunnel; and inserting a transverse pin through the second hole to secure one end of the replacement ligament to the femur.

11. The method of claim 10, further comprising the step of inserting a guide pin through the tibia and the femur to establish the position of a ligament tunnel prior to the step of drilling the first hole through the bone to form the ligament tunnel.

12. The method of claim 10, further comprising the steps of:

drilling a third hole in the tibia at an angle relative to the ligament tunnel using the drill inside the ligament tunnel as a support to establish the position of the third hole; and inserting a transverse pin through the third hole to secure a second end of the replacement ligament to the tibia.

13. A method for locating and installing a transverse pin for holding a ligament replacement in a tunnel formed in adjacent jointed bones with the pin intersecting the tunnel and the ligament replacement inserted in the tunnel, the method comprising the steps of:

inserting a guide pin through said adjacent bones to define a centerline of the tunnel;

drilling the tunnel with a cannulated drill using the guide pin as a center guide for the cannulated drill;

installing a drill guide on the drill used in the tunnel drilling step, the drill guide being rotatable about a longitudinal drilling axes of the drill and longitudinal axis of the guide pin, said drill guide having a first arm journal end mounted on the drill and a second arm extending away from the first arm and at an angle thereto and having a transverse drill guide opening having a drill axis intersecting the longitudinal centerline axes of the guide pin and tunnel drill;

adjusting the position of the drill guide longitudinally on the drill to position the drill axis of the transverse guide opening relative to the tunnel properly to intersect the ligament replacement in one of the adjacent bones in the tunnel;

pivotally adjusting the position of the drill guide about the longitudinal centerline axes of the drill and guide pin to find the desired anatomical location for inserting the transverse pin into the tunnel;

using the drill guide for aligning a second drill to drill transversely into the bone to provide a transverse guide hole with a centerline axis;

inserting and positioning the ligament replacement into the tunnel drilled by the cannulated drill so as to be intersected by the centerline axis of the transverse guide hole; and inserting the transverse pin through the guide hole, the tunnel, the ligament replacement therein, and on into the opposite side of the tunnel to anchor the ligament replacement in the tunnel.

14. The method of claim 13, including locating and installing a second transverse pin in the adjacent bone intersecting the tunnel and ligament replacement, the method further comprising the steps of:

pivotally adjusting the position of the drill guide on the cannulated drill and about the centerline axes of the cannulated drill and guide pin to find a desired anatomical location for inserting the second transverse pin into the adjacent bone;

drilling transversely into the adjacent bone to provide a second transverse guide hole in the adjacent bone; and inserting the second transverse pin through the guide hole in the adjacent bone, the tunnel, the ligament replacement therein and on into an opposite side of the tunnel to anchor the ligament replacement in the adjacent bone.

* * * * *